US011485694B2

(12) United States Patent
Zhang et al.

(10) Patent No.: US 11,485,694 B2
(45) Date of Patent: Nov. 1, 2022

(54) DEALKLYLATION AND TRANSALKYLATION OF MIXED PHENOLS TO MAKE CRESOLS

(71) Applicants: China Petroleum & Chemical Corporatoin, Beijing (CN); UOP LLC, Des Plaines, IL (US)

(72) Inventors: Shuguang Zhang, Wilmette, IL (US); Lubo Zhou, Deer Park, IL (US)

(73) Assignees: China Petroleum & Chemical Corporation, Beijing (CN); UOP LLC, Des Plaines, IL (US)

( * ) Notice: Subject to any disclaimer, the term of this patent is extended or adjusted under 35 U.S.C. 154(b) by 0 days.

(21) Appl. No.: 17/258,337

(22) PCT Filed: Feb. 4, 2019

(86) PCT No.: PCT/US2019/016533
§ 371 (c)(1),
(2) Date: Jan. 6, 2021

(87) PCT Pub. No.: WO2020/162876
PCT Pub. Date: Aug. 13, 2020

(65) Prior Publication Data
US 2021/0139399 A1    May 13, 2021

(51) Int. Cl.
*C07C 37/48* (2006.01)
*C07C 37/50* (2006.01)
*C07C 37/00* (2006.01)

(52) U.S. Cl.
CPC ............. *C07C 37/48* (2013.01); *C07C 37/50* (2013.01); *C07C 37/006* (2013.01); *C07C 37/007* (2013.01)

(58) Field of Classification Search
CPC ....... C07C 37/48; C07C 37/50; C07C 37/006; C07C 37/007
See application file for complete search history.

(56) References Cited

U.S. PATENT DOCUMENTS

| 1,947,648 A | 2/1934 | Hofmann et al. |
| 1,980,384 A | 11/1934 | Comte |
| 2,095,801 A | 10/1937 | Engel |
| 2,295,672 A | 9/1942 | Meharg et al. |

(Continued)

FOREIGN PATENT DOCUMENTS

| CA | 910920 A | 9/1972 | |
| EP | 0905114 A1 * | 3/1999 | ............. C07C 37/48 |

(Continued)

OTHER PUBLICATIONS

International Search Report from PCT application No. PCT/IB2019/016533 dated Aug. 19, 2019.

(Continued)

*Primary Examiner* — Rosalynd A Keys

(57) ABSTRACT

Processes of producing cresols from a phenols containing feed are described. The processes involve a combination of dealkylation and transalkylation processes. The dealkylation process converts the heavy alkylphenols in an alkylphenols stream to phenol and olefins. The olefins produced in the dealkylation process are separated out. The methylphenols, which are not converted in the dealkylation process, and phenol react in the transalkylation process to generate cresols.

19 Claims, 1 Drawing Sheet

(56) References Cited

U.S. PATENT DOCUMENTS

| | | |
|---|---|---|
| 2,310,616 A | 2/1943 | Cislak et al. |
| 2,514,960 A | 7/1950 | Luten, Jr. et al. |
| 2,553,538 A * | 5/1951 | Arnold .................... C07C 37/16 |
| | | 568/783 |
| 2,684,389 A | 7/1954 | Offutt |
| 2,777,881 A | 1/1957 | Neuworth |
| 2,998,457 A | 11/1958 | Paulsen |
| 3,091,646 A | 5/1963 | Leston |
| 3,284,513 A | 11/1966 | Dedinas et al. |
| 3,284,514 A | 11/1966 | Dedinas et al. |
| 3,296,316 A | 6/1967 | Neuworth |
| 3,417,149 A | 12/1968 | Neuworth |
| 3,692,846 A | 9/1972 | Dalman et al. |
| 3,737,466 A * | 6/1973 | Sharp .................... C07C 37/16 |
| | | 568/804 |
| 3,933,927 A | 1/1976 | Goodard |
| 4,060,560 A | 11/1977 | Leach |
| 4,110,253 A | 8/1978 | Leach |
| 4,110,544 A | 8/1978 | Goodwin et al. |
| 4,149,019 A | 4/1979 | Alscher et al. |
| 4,150,243 A | 4/1979 | Brück et al. |
| 4,267,391 A | 5/1981 | Leston |
| 4,325,789 A * | 4/1982 | Wust .................... C07C 37/78 |
| | | 203/67 |
| 4,431,850 A | 2/1984 | Huibers et al. |
| 4,476,329 A | 10/1984 | Chambers et al. |
| 4,533,767 A | 8/1985 | Talley |
| 4,554,388 A | 11/1985 | Keim et al. |
| 4,590,306 A | 5/1986 | Korff et al. |
| 4,605,790 A | 8/1986 | Wojtkowski |
| 6,512,149 B2 | 1/2003 | Yao et al. |

FOREIGN PATENT DOCUMENTS

| | | |
|---|---|---|
| GB | 1238353 | 7/1971 |
| GB | 1444935 | 8/1976 |
| SU | 268434 A1 | 10/1970 |
| SU | 1004342 A1 | 3/1983 |
| SU | 1721043 A1 | 3/1992 |

OTHER PUBLICATIONS

Written Opinion from PCT application No. PCT/IB2019/016533 dated Aug. 19, 2019.
Fardhyanti, Dewi S. et al., Extraction of Phenol, o-Cresol, and p-Cresol from Coal Tar Extract: Effect of Temperature and Mixing, World Academy of Science, Engineering and Technology, International Journal of Chemical and Molecular Engineering, vol. 7., No. 6, 2013.
Zhu, X et al., Role of Transalkylation reactions in the conversion of anisole over HZSM-5, Applied Catalysis A General 379 (2010) 172-182.
Janardanarao, Mulpurl, Cracking and Hydrogenation of Low-Temperature Coal Tars and Alkyl Phenols, Ind. Eng. Chem. Prod. Res Dev. 1982, 21, 375-390.
International Preliminary Report on Patentability from PCT application No. PCT/IB2019/016533 dated Aug. 19, 2021.
Search Report from corresponding Russian application No. 2021120490, dated Jul. 13, 2022.

* cited by examiner

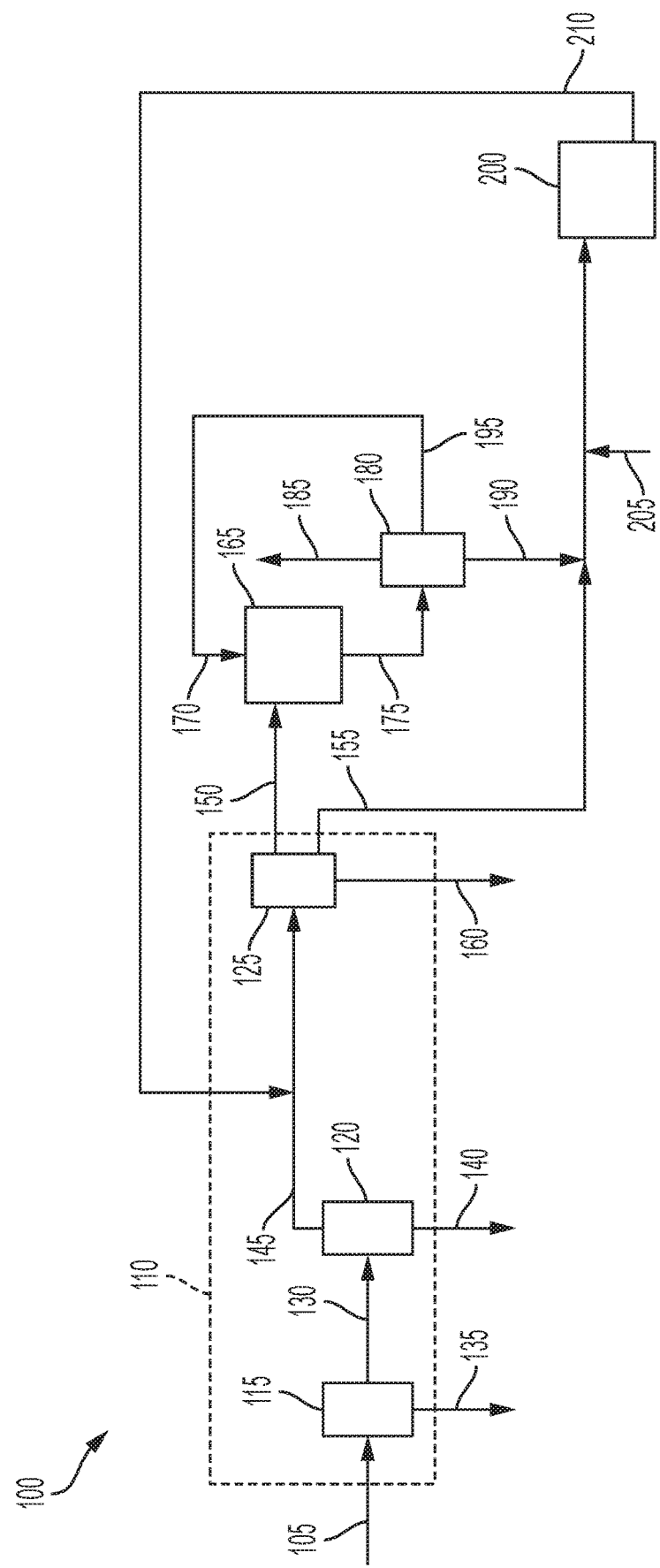

DEALKLYLATION AND TRANSALKYLATION OF MIXED PHENOLS TO MAKE CRESOLS

This application is a U.S. National Phase under 35 U.S.C. § 371 of International Application No. PCT/US2019/016533 filed Feb. 4, 2019.

BACKGROUND OF THE INVENTION

Many possible feeds may include significant amounts of phenols which can be difficult to recover in a cost effective manner. For example, low and mid temperature coal tars are usually rich in phenolic compounds. Sometimes the content can be close to about 40 wt % of the coal tar stream. These phenols may be extracted from coal tar using various methods, such as washing with aqueous sodium hydroxide solution followed by neutralization with sulfuric acid or carbon dioxide, solvent extraction, pressurized crystallization, etc. The composition of the crude phenols obtained, however, is very complicated. For example, the phenols mixture extracted from the fraction with boiling range from 170 to 240° C. of one heavy coal tar contains 60 types of phenols, most of which have concentrations lower than 1 wt % of the whole coal tar, as disclosed by the paper authored by Wang, et al., "Extraction and GC/MS analysis of phenolic compounds in low temperature coal tar from Northern Shaanxi", J. of China Coal Society, 36 (4) (2011), 664-669. Some of these phenols also have very similar boiling points. This makes their separation and purification extremely difficult. In addition, only certain phenols, such as phenol, cresols, xylenols, naphthols and possibly methylnaphthols, have high volumes, have been widely used, and are therefore of economic interest.

Therefore, there is a need for a method of processing coal tar and other phenols containing feeds to obtain phenol and cresols in a cost effective manner.

BRIEF DESCRIPTION OF THE DRAWINGS

The FIGURE illustrates one embodiment of a process according to the present invention.

DESCRIPTION OF THE INVENTION

It is desirable to be able to process materials containing significant amounts of phenols, including phenol and cresols to recover phenols from those materials. By phenol containing feed streams we mean any hydrocarbonaceous or aqueous streams from pharmaceutical, chemical, or petroleum processes, which contain phenols in the range of 0.1 to 100 wt %, or 0.1 to 80%, or 0.1 to 60%, or 0.1 to 40%, or 1 to 40%, or 5 to 40%, or 5 to 30%. Suitable phenol containing feed stream include, but are not limited to, product streams like coal tar, light oil, bio-oil from the gasification and liquefaction of coal, wood, plant oil, and other biomass materials.

The alkylphenols in a crude phenols mixture can be converted to cresols, and/or methylnaphthols/naphthols for easy separation and utilization. Olefins such as ethylene, propylene, and butenes, are also produced. This is done by coupling dealkylation and transalkylation processes. The dealkylation process is designed to convert the heavy alkylphenols in an alkylphenol stream to phenol, methylphenols and olefins. By "heavy alkylphenols," we mean alkylphenols having alkyl groups containing two or more carbons, such as ethylphenols, propylphenols. By "alkylphenols," we mean methylphenols (including mono-methyl, di-methyl, and multi-methyl phenols) and heavy alkylphenols (phenols having alkyl groups with two or more carbon atoms). Most of the methylphenols, such as cresols, xylenols and multi-methyl phenols remain intact following the dealkylation process. The olefins produced in the dealkylation process are separated out. The methylphenols and phenol react in a transalkylation process to generate cresols.

The dealkylation process removes the alkyl side chains from the alkylphenols primarily alkyl groups having two or more carbon atoms. Dealkylation of methylphenols is very difficult compared to other alkylphenols. Studies have shown that the logarithms of the rate constants of dealkylation of alkylbenzene and alkylphenol have a fine linear relationship with the enthalpy change for the hydride abstraction from paraffins in a wide range. This indicates that the methyl group will be extremely difficult to remove compared to longer alkyl groups. For example, the demethylation rate of o-cresol would be 0.1% of the deethylation rate of o-ethylphenol if the linear relation is extrapolated, as published by Mochida et al., "Linear free energy relationships in heterogeneous catalysis I. Dealkylation of alkylbenzenes on cracking catalysts", J. Catal., 7 (1967), 386-392. Studies of dealkylation of alkylphenols on an acid catalyst have shown that the rate of dealkylation is greater with the propyl group than with the ethyl group, but further lengthening of the chain has no more effect. Studies have also shown that phenols with branched alkyls dealkylate faster than the corresponding normal form, as reported by Kraus et al., "Effects of structure on rate in reactions of organic compounds over solid catalysts", Proc. Intern. Congr. Catalysis, 3rd, Amsterdam, 1964, p. 557.

Dealkylation can be done with or without catalyst. Alkylphenols can be dealkylated through thermal cracking at high temperature without catalyst. Dealkylation without a catalyst can be quite energy intensive because the temperature is in the range of 400 to 900° C., often 700 to 900° C. Furthermore, it is often not selective due to the loss of the hydroxyl group.

Catalytic dealkylation of heavy alkylphenols can be done at much milder conditions. Typical temperatures range from 100 to 700° C., or 200 to 540° C. Ethylphenols and propylphenols can be dealkylated at temperatures from 300 to 400° C., for example, to produce phenol and ethylene/propylene on a ZSM-5 zeolite. Debutylation of alkylphenols has also been reported on acidic clay catalyst. Any suitable dealkylation catalyst can be used, including, but not limited to, silica alumina, zeolites, gamma alumina, chromium oxide, other oxides or mixed oxides, or combinations thereof.

Pressures for dealkylation are generally in the range of 1-5 MPa(a). Dealkylation reactions can also performed under vacuum, for example, typically 50 kPa(a), with a maximum of 20 kPa(a). The weight hourly space velocity (WHSV) typically ranges from 1 to 5 $hr^{-1}$.

Water/steam may be co-fed to prevent severe catalyst deactivation. Dealkylation is normally conducted in superheated steam. Typical steam to alkylphenol molar ratios range from 0.1:1 to 10:1, or 1:1 to 8:1.

Hydrogen can be co-fed to the dealkylation reaction zone to minimize catalyst deactivation. Hydrogen to phenols ratios typically range from 0.1:1 to 10:1, or 1:1 to 4:1.

Other co-feeds include, but are not limited to, polar inert compounds such as benzene. Typical benzene to alkylphenol molar ratios range from 0.1:1 to 10:1, or 1:1 to 8:1.

Dealkylation of the heavy alkylphenols yields phenol, cresols, heavy methylphenols (phenols with more than one methyl group), and olefins.

The dealkylation effluent is separated into an olefin stream and a phenols stream comprising phenol, cresols, heavy methylphenols, and unreacted heavy alkylphenols.

The phenol and heavy methylphenols in the phenols stream are then transalkylated to form cresols. Transalkylation is a chemical reaction resulting in transfer of an alkyl group from one organic compound to another. Catalysts, particularly zeolite catalysts, are often used to effect the reaction. If desired, the transalkylation catalyst may be metal stabilized using a noble metal or base metal, and may contain suitable binder or matrix material such as inorganic oxides and other suitable materials. In a transalkylation process, a multi-alkylaromatic hydrocarbon feed and an aromatic hydrocarbon feed are provided to a transalkylation reaction zone. The feed is usually heated to reaction temperature and then passed through a reaction zone, which may comprise one or more individual reactors. Passage of the combined feed through the reaction zone produces an effluent stream comprising unconverted feed and product monoalkylated hydrocarbons.

The transalkylation reaction can be effected in contact with a catalytic composite in any conventional or otherwise convenient manner and may comprise a batch or continuous type of operation, with a continuous operation being preferred. The transalkylation catalyst is usefully disposed as a fixed bed in a reaction zone of a vertical tubular reactor, with the alkylaromatic feed stock charged through the bed in an upflow or downflow manner.

For transalkylation, the temperature is typically in the range of 50-700° C., or 200-540° C. The transalkylation zone is typically operated at pressures ranging from about 100 kPa(a) to 6 MPa(a). The WHSV is generally in the range of 0.1 to 20 $hr^{-1}$, or 0.1 to 10 $hr^{-1}$.

The catalyst is typically selected to have relatively high stability at a high activity level. Suitable transalkylation catalysts include, but are not limited to zeolites, acidic clay, silica alumina, acidic resins, mixed metal oxides, and the like as are known in the art.

The ratio of phenol to methyl groups should be 1:1 or higher. The presence of additional phenol improves the reaction kinetics. If the process does not provide or generate sufficient phenol, it may be necessary to add fresh phenol.

For example, the transalkylation of heavy methylphenols with phenols to produce cresols and xylenols has been reported on zeolite catalyst around 350° C. by Moeketsi, K., M. S. thesis, "Transalkylation of higher methylphenols with phenol to produce cresols and xylenols", Univ. of Cape Town, May 2007.

The transalkylation effluent stream comprises cresols, unreacted phenol and heavy methylphenols and heavy alkylphenols, and is recycled to the crude phenol feed.

One aspect of the invention is a process of producing cresols from a phenols containing feed. In one embodiment, the process comprises: introducing the phenols containing feed stream into a first separation zone, where it is separated in the first separation zone into at least a phenol stream comprising phenol, an alkylphenol stream comprising heavy methyl phenols and heavy alkylphenols, and a cresols stream comprising cresols. The heavy alkylphenols in the alkylphenols stream are dealkylated in a dealkylation reaction zone under dealkylation conditions to produce a dealkylation effluent stream comprising phenol, cresols, heavy methyl phenols, and olefins. The dealkylation effluent stream is separated in a dealkylation separation zone into at least an olefin stream comprising olefins, and a second stream comprising phenol, cresols, and heavy methyl phenols. The second stream is transalkylated in a transalkylation reaction zone under transalkylation conditions to produce a transalkylation effluent stream comprising cresols, unreacted phenol, unreacted heavy alkylphenols, and unreacted heavy methyl phenols. One or more of: at least a portion of the phenol stream, the olefin stream, or the cresols stream are recovered.

In some embodiments, the process further comprises: recycling the transalkylation effluent stream to the first separation zone.

In some embodiments, the process further comprises: passing the phenol stream from the first separation zone to the transalkylation reaction zone.

In some embodiments, separating the phenols containing feed stream comprises separating a phenol stream comprising phenol and alkylphenols from the phenols containing feed stream by extraction.

In some embodiments, the process further comprises: fractionating the phenols containing feed stream before separating the extracted stream.

In some embodiments, the process further comprises: fractionating the extracted phenol stream into at least the phenol stream, the alkylphenol stream, and the cresols stream.

In some embodiments, the process further comprises purifying the cresols stream.

In some embodiments, separating the dealkylation effluent stream comprises: fractionating the dealkylation effluent stream into at least the olefin stream and the second stream.

In some embodiments, the process further comprises: passing fresh phenol to the transalkylation reaction zone.

In some embodiments, the dealkylation reaction conditions comprise at least one of: a temperature in a range of 100-700° C. in the presence of a catalyst; a temperature in a range of 400-900° C. in the absence of a catalyst; a pressure in a range of 1-5 MPa(a); or a WHSV of 1-5 $h^{-1}$.

In some embodiments, the transalkylation reaction conditions comprise at least one of: a temperature in a range of 50-700° C. in the presence of a catalyst; a pressure in a range of 100 kPa(a) to 6 MPa(a); or a WHSV in a range of 0.1-20 $h^{-1}$.

In some embodiments, dealkylating the heavy alkylphenols is performed in the presence of a catalyst, or transalkylating the second stream is performed in the presence of a catalyst, or both.

In some embodiments, the process further comprising introducing one or more of: a water or steam stream, a hydrogen stream, or benzene stream to the dealkylation reaction zone.

In some embodiments, fractionating the phenols containing feed stream comprises: fractionating the phenols containing feed stream into a stream comprising components having a boiling below 245° C. and a stream comprising components having a boiling above 245° C. further comprising one or more of: recovering naphthols from the stream comprising components having a boiling above 245° C.; hydroprocessing the stream comprising components having a boiling above 245° C.; or dealkylating at least a portion of the stream comprising components having a boiling above 245° C. to form a dealkylated stream and transalkylating at least a portion of the dealkylated stream.

In some embodiments, the phenols containing feed stream comprises one or more of: a coal tar feed stream, a wood feed stream, a biomass feed stream, and a lignin feed stream.

Another aspect of the invention is a process of producing cresols from a phenols containing feed. In one embodiment, the process comprises: introducing a phenols containing feed stream into a first separation zone and separating the phenols containing feed stream in the first separation zone into at least a phenol stream comprising phenol, an alkylphenol stream comprising heavy methyl phenols and heavy alkylphenols, and a cresols stream comprising cresols. The heavy alkylphenols in the alkylphenols stream are dealkylated in a dealkylation reaction zone under dealkylation conditions to produce a dealkylation effluent stream comprising phenol, cresols, heavy methyl phenols, and olefins. The dealkylation effluent stream is separated in a dealkylation separation zone into at least an olefin stream comprising olefins, and a second stream comprising phenol, cresols, and heavy methyl phenols. The second stream is transalkylated in a transalkylation reaction zone under transalkylation conditions to produce a transalkylation effluent stream comprising cresols, unreacted phenol, unreacted heavy alkylphenols, and unreacted heavy methyl phenols. The transalkylation effluent stream is recycled to the separation zone. One or more of: at least a portion of the phenol stream, the olefin stream, or the cresol stream are recovered.

In some embodiments, separating the phenols containing feed stream comprises: separating an extracted phenol stream comprising phenol and alkylphenols from the phenols containing feed stream by extraction; fractionating the extracted phenol stream into at least the phenol stream, the alkylphenol stream, and the cresols stream; and optionally, fractionating the phenols containing feed stream before extracting the extracted phenol stream.

In some embodiments, the dealkylation reaction conditions comprise at least one of: a temperature in a range of 100-700° C. in the presence of a catalyst; a temperature in a range of 700-900° C. in the absence of a catalyst; a pressure in a range of 1-5 MPa(a); or an WHSV of 1-5 $h^{-1}$.

In some embodiments, the transalkylation reaction conditions comprise at least one of: a temperature in a range of 50-700° C. in the presence of a catalyst; a pressure in a range of 100 kPa(a) to 6 MPa(a); or a WHSV of 0.1-20 $h^{-1}$.

In some embodiments, dealkylating the heavy alkylphenols is performed in the presence of a catalyst, or transalkylating the second stream is performed in the presence of a catalyst, or both.

The FIGURE illustrates one embodiment of a process 100. For convenience, the process 100 will be discussed using a coal tar feed stream 105. Those of skill in the art will recognize that other phenol containing feeds could also be used. The coal tar feed stream 105 containing phenols is sent to the feed separation zone 110. In the embodiment shown in the FIGURE, the feed separation zone 110 includes a first fractionation zone 115, an extraction zone 120, and a second fractionation zone 125. The coal tar feed stream 105 is fractionated in the first fractionation zone 115. The fraction 130 with a boiling point below 245° C. at atmospheric pressure is fed to the extraction zone 120, while the fraction 135 with a boiling point above 245° C. may be sent for further processing.

The fraction 130 is separated in the extraction zone 120 into a hydrocarbon stream 140 and an extracted phenol stream 145. The hydrocarbon stream 140 can be sent for further processing or combined with fraction 135.

The extracted phenol stream 145 comprises phenol and alkylphenols. The extracted phenol stream 145 is sent to the second fractionation zone 125 where it is separated into a heavy alkylphenol stream 150 comprising heavy alkylphenols and heavy methylphenols, a phenol stream 155 comprising phenols, and a cresols stream 160 comprising cresols.

The heavy alkylphenol stream 150 is fed to a dealkylation reaction zone 165. The reaction conditions are controlled so that mainly alkyl groups with two or more carbons are removed, while methyl and hydroxyl groups remain. A steam stream 170 is fed to the dealkylation reaction zone 165 to maintain catalyst activity.

The dealkylation effluent 175 comprises phenol, heavy methyl phenols, and olefins, as well as unreacted heavy alkylphenols. The dealkylation effluent 175 is sent to a dealkylation separation zone 180 where it is separated into an olefin stream 185 comprising olefins and second stream 190 comprising phenol, heavy methylphenols, and unreacted heavy alkylphenols. The dealkylation effluent 175 may also contain water, which can be separated out as water stream 195 and recycled to the dealkylation reaction zone 165.

The second stream 190 is sent to the transalkylation reaction zone 200, along with phenol stream 155. Optionally, depending on the content of methyl groups in the heavy methyl phenols, a fresh phenol stream 205 can be sent to transalkylation reaction zone 200, if needed. There should be enough phenol to react with the heavy methyl phenols to form cresols.

The transalkylation effluent stream 210 comprising cresols is sent to the separation zone 110 where it is combined with the extracted phenol stream 145 and sent to the second fractionation zone 125.

Further processing of the cresols in cresol stream 160 can be done through purification using technology such as distillation, crystallization, and/or extraction to obtain higher value isomer, such as m-cresol, for example.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As depicted, process flow lines in the figures can be referred to, interchangeably, as, e.g., lines, pipes, branches, distributors, streams, effluents, feeds, products, portions, catalysts, withdrawals, recycles, suctions, discharges, and caustics.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process of producing cresols from a phenols containing feed comprising:

introducing the phenols containing feed stream into a first separation zone;

separating the phenol containing feed stream in the first separation zone into at least a phenol stream comprising phenol, an alkylphenol stream comprising heavy methyl phenols and heavy alkylphenols, and a cresols stream comprising cresols, wherein the heavy alkylphenols comprise alkylphenols having alkyl groups containing 2 or more carbon atoms;

dealkylating the heavy alkylphenols in the alkylphenols stream in a dealkylation reaction zone in the presence of a dealkylation catalyst under dealkylation conditions to produce cresols, phenol, heavy methyl phenols, and olefins forming a dealkylation effluent stream comprising the phenol, the cresols, the heavy methyl phenols, and the olefins;

separating the dealkylation effluent stream in a dealkylation separation zone into at least an olefin stream comprising the olefins, and a second stream comprising the phenol, the cresols, and the heavy methyl phenols;

introducing the phenol stream from the first separation zone and the second stream from the dealkylation separation zone to the transalkylation reaction zone;

transalkylating the phenol and the heavy methyl phenols in the second stream and the phenol in the phenol stream from the first separation zone in a, transalkylation reaction zone in the presence of a transalkylation catalyst under transalkylation conditions to produce additional cresols forming a transalkylation effluent stream comprising the additional cresols, unreacted phenol, unreacted heavy alkylphenols, and unreacted heavy methyl phenols; and recovering the cresols stream and optionally the olefin stream, or at least a portion of the phenol stream, or both.

2. The process of claim 1 further comprising:
recycling the transalkylation effluent stream to the first separation zone.

3. The process of claim 1 wherein separating the phenols containing feed stream comprises separating a phenol stream comprising phenol and alkylphenols from the phenols containing feed stream by extraction.

4. The process of claim 3 further comprising:
fractionating the phenols containing feed stream before separating the extracted stream.

5. The process of claim 3 further comprising:
fractionating the extracted phenol stream into at least the phenol stream, the alkylphenol stream, and the cresols stream.

6. The process of claim 4 wherein fractionating the phenols containing feed stream comprises:
fractionating the phenols containing feed stream into a stream comprising components having a boiling below 245° C. and a stream comprising components having a boiling point above 245° C. further comprising one or more of:
recovering naphthols from the stream comprising components having a boiling above 245° C.;
hydroprocessing the stream comprising components having a boiling above 245° C.; or
dealkylating at least a portion of the stream comprising components having a boiling point above 245° C. to form a dealkylated stream and transalkylating at least a portion of the dealkylated stream.

7. The process of claim 5 further comprising purifying the cresols stream.

8. The process of claim 1 wherein separating the dealkylation effluent stream comprises:
fractionating the dealkylation effluent stream into at least the olefin stream and the second stream.

9. The process of claim 1 further comprising:
passing fresh phenol to the transalkylation reaction zone.

10. The process of claim 1 wherein the dealkylation reaction conditions comprise at least one of: a temperature in a range of 100-700° C.; a pressure in a range of 1-5 MPa(a); or a WHSV of 1-5 $h^{-1}$.

11. The process of claim 1 wherein the transalkylation reaction conditions comprise at least one of: a temperature in a range of 50-700° C.; a pressure in a range of 100 kPa(a) to 6 MPa(a); or a WHSV in a range of 0.1-20 $h^{-1}$.

12. The process of claim 1 further comprising introducing one or more of: a water or steam stream, a hydrogen stream, or a benzene stream to the dealkylation reaction zone.

13. The process of claim 1 wherein the phenols containing feed stream comprises one or more of: a coal tar feed stream, light oil, or a bio-oil feed stream.

14. A process of producing cresols from a phenols containing feed comprising:
introducing a phenols containing feed stream into a first separation zone;
separating the phenols containing feed stream in the first separation zone into at least a phenol stream comprising phenol, an alkylphenol stream comprising heavy methyl phenols and heavy alkylphenols, and a cresols stream comprising cresols, wherein the heavy alkylphenols comprise alkylphenols having alkyl groups containing 2 or more carbon atoms;
dealkylating the heavy alkylphenols in the alkylphenols stream in a dealkylation reaction zone in the presence of a dealkylation catalyst under dealkylation conditions to produce cresols, phenol, heavy methyl phenols, and olefins forming a dealkylation effluent stream comprising the phenol, the cresols, the heavy methyl phenols, and the olefins;
separating the dealkylation effluent stream in a dealkylation separation zone into at least an olefin stream comprising the olefins, and a second stream comprising the phenol, the cresols, and the heavy methyl phenols;
introducing the phenol stream from the first separation zone and the second stream from the dealkylation separation zone to the transalkylation reaction zone;
transalkylating the phenol and the heavy methyl phenols in the second stream and the phenol in the phenol stream in a transalkylation reaction zone in the presence of a transalkylation catalyst under transalkylation conditions to produce additional cresols forming a transalkylation effluent stream comprising the additional cresols, unreacted phenol, unreacted heavy alkylphenols, and unreacted methyl phenols;
recycling the transalkylation effluent stream to the first separation zone; and
recovering the cresols stream and one or more of: at least a portion of the phenol stream, or the olefins stream.

15. The process of claim 14 wherein separating the phenols containing feed stream comprises:
separating an extracted phenol stream comprising phenol and alkylphenols from the phenols containing feed stream by extraction;
fractionating the extracted phenol stream into at least the phenol stream, the alkylphenol stream, and the cresols stream; and
optionally, fractionating the phenols containing feed stream before extracting the extracted phenol stream.

16. The process of claim 14 wherein the dealkylation reaction conditions comprise at least one of: a temperature in a range of 100-700° C.; a pressure in a range of 1-5 MPa(a); or a WHSV of 1-5 $h^{-1}$.

17. The process of claim 14 wherein the transalkylation reaction conditions comprise at least one of: a temperature in a range of 50-700° C.; a pressure in a range of 100 kPa(a) to 6 MPa(a); or a WHSV of 0.1-20 h$^{-1}$.

18. The process of claim 1 wherein the dealkylation catalyst comprises silica alumina, zeolites, gamma alumina, chromium oxide, other oxides or mixed oxides, or combinations thereof, and wherein the transalkylation catalyst comprises zeolites, acidic clay, silica alumina, acidic resins, and mixed metal oxides.

19. The process of claim 14 wherein the dealkylation catalyst comprises silica alumina, zeolites, gamma alumina, chromium oxide, other oxides or mixed oxides, or combinations thereof, and wherein the transalkylation catalyst comprises zeolites, acidic clay, silica alumina, acidic resins, and mixed metal oxides.

\* \* \* \* \*